United States Patent [19]
Colvin et al.

[11] Patent Number: 6,066,160
[45] Date of Patent: May 23, 2000

[54] PASSIVE KNOTLESS SUTURE TERMINATOR FOR USE IN MINIMALLY INVASIVE SURGERY AND TO FACILITATE STANDARD TISSUE SECURING

[75] Inventors: Stephen Colvin; Eugene Grossi, both of New York; Allan Katz; Paul Oddo, both of Freeport, all of N.Y.

[73] Assignee: Quickie LLC, New York, N.Y.

[21] Appl. No.: 09/198,087

[22] Filed: Nov. 23, 1998

[51] Int. Cl.[7] .................................................. A61B 17/04
[52] U.S. Cl. ............................. 606/232; 606/151; 24/129
[58] Field of Search ................................... 606/232, 151; 24/115 R, 129 R

[56] References Cited

U.S. PATENT DOCUMENTS

| | | |
|---|---|---|
| 3,143,742 | 8/1964 | Cromie . |
| 3,541,591 | 11/1970 | Hoegerman ............................ 606/232 |
| 3,859,668 | 1/1975 | Anderson . |
| 3,898,999 | 8/1975 | Haller . |
| 3,976,079 | 8/1976 | Samuels . |
| 3,996,623 | 12/1976 | Kaster . |
| 4,743,253 | 5/1988 | Magladry . |
| 4,823,794 | 4/1989 | Pierce ..................................... 606/232 |
| 4,863,460 | 9/1989 | Magladry . |
| 4,955,913 | 9/1990 | Robinson . |
| 5,053,047 | 10/1991 | Yoon . |
| 5,071,431 | 12/1991 | Sauter . |
| 5,074,874 | 12/1991 | Yoon et al. . |
| 5,078,731 | 1/1992 | Hayhurst ................................. 606/232 |
| 5,116,840 | 5/1992 | Ganguly et al. . |
| 5,123,913 | 6/1992 | Wilk . |
| 5,163,954 | 11/1992 | Curcio . |
| 5,171,251 | 12/1992 | Bregen . |
| 5,282,832 | 2/1994 | Toso . |
| 5,306,290 | 4/1994 | Martins et al. ......................... 606/232 |
| 5,306,296 | 4/1994 | Wright . |
| 5,391,173 | 2/1995 | Wilk ........................................ 606/232 |
| 5,409,499 | 4/1995 | Yi . |
| 5,445,167 | 8/1995 | Yoon et al. ............................. 606/232 |
| 5,474,572 | 12/1995 | Hayhurst ................................. 606/232 |
| 5,496,336 | 3/1996 | Cosgrove . |
| 5,531,763 | 7/1996 | Mastri . |
| 5,681,351 | 10/1997 | Jamiolkowski . |
| 5,776,188 | 7/1998 | Shepherd . |

*Primary Examiner*—Gary Jackson
*Attorney, Agent, or Firm*—Pepe & Hazard

[57] ABSTRACT

A suture securing apparatus comprising an apparatus body having a upper surface, a lower surface, an outer surface, and at least one aperture, the aperture having a longitudinal axis extending from the upper surface to the lower surface and defining an aperture surface, wherein a first longitudinal direction and a second longitudinal direction thereof each extends along the longitudinal axis in opposite directions, the aperture including an integral locking means for engaging a suture threaded therethrough.

34 Claims, 6 Drawing Sheets

PASSIVE KNOTLESS SUTURE TERMINATOR FOR USE IN MINIMALLY INVASIVE SURGERY AND TO FACILITATE STANDARD TISSUE SECURING

FIELD OF THE INVENTION

The instant invention relates to apparatus and systems for use in securing prosthetics to native tissue or tissue to native tissue in medical procedures. More particularly, this invention relates to apparatus and systems which facilitate securing the ends of standard sutures which can be used to secure tissues to native tissue or prosthetic devices to native tissue without requiring activation of the device.

BACKGROUND OF THE INVENTION

Suturing is an integral part of surgery. It is used to hold tissues together or to secure prosthetics (including but not limited to, heart valve prosthetics, annuloplasty rings, vascular grafts, and orthopedic implants) to native tissue. Sutures have conventionally been used to fasten such implants. The suture material is passed through the native tissue and then through part of the prosthetic or adjacent native tissue. The two are then drawn and secured together by tying a knot on the end of the suture.

By way of example, heart valve replacements and prostheses have been used for many years and many improvements in both the functionality and ease of implantation have been made thereon. More precisely, during conventional heart valve replacement surgery, sutures are placed in the native annulus after removal of a damaged native valve. Often small pledgets are threaded on the sutures to buttress their contact with the native tissue. The suture is then inserted through the suture ring of the replacement heart valve. Knots are then tied on the sutures to secure the replacement heart valve to the native heart annulus in its desired position such that there will be no leakage around the replacement heart valve.

When it is recognized that each of the completed knots used to secure the replacement heart valve to the native annulus is actually composed of six or more individual knots, it will be appreciated that this task would take a surgeon a significant amount of time to secure the replacement heart valve into position. Further, with the increased level of difficulty associated with this process, comes an increase in the likelihood of error by the surgeon. In addition, since the incision must be larger and the procedure requires greater time, the patient is exposed to collateral risk factors (which include, but are not limited to, an increased incidence of infection, hypothermia, and fluid loss).

Traditionally, the conventional prosthetic attachment procedure has required the surgeon to possess great dexterity and to be in close proximity to the knot. Emerging minimally invasive surgical techniques add an extra level of difficulty to this task since the incisions associated with such methods are generally much smaller than in conventional surgery. As a result, surgeons are required to spend more time tying off the sutures, or in some cases are required to stretch the incision in order to complete the task. By requiring the surgeon to make larger incisions to gain access to tie these knots, the advantages commonly associated with these minimally invasive surgical procedures, of quicker healing, less disruption to surrounding tissues, and less likelihood of infection, are jeopardized.

Sensitive to these new demands, methods and apparatus for implanting heart valve replacement apparatus under minimally invasive conditions have been developed. Examples of such replacement apparatus and methods for implanting heart valve replacement apparatus have been disclosed in U.S. Pat. Nos. 4,655,773; 4,364,126; 4,204,283; 3,898,999; 3,996,623; 3,859,668; 3,534,411; and 5,776,188. Indeed, apparatus and methods have been disclosed that avoid the use of sutures altogether. For example, U.S. Pat. No. 3,143,742 discloses spacing curved pins along the circumference of the apparatus to pierce the tissue of the native annulus of the heart at the desired attachment point. Unfortunately, due to vagaries in the native tissue, good coaptation along a geometrically perfect surface is not always possible.

Novel technologies have been deployed for the purpose of sewing heart valve subcomponents together. U.S. Pat. Nos. 5,071,431; 4,863,460; and 4,743,253 each use a ductile or deformable locking ring as a means to bind the various subcomponents of the heart valve device. However, the aforementioned approaches do not avoid the securing of the implant to the native tissue without the use of traditional suturing methods.

Recently, medical instruments have been developed, which permit surgeons to manipulate sutures through a small opening. However, these instruments, which provide an extension between the surgeon's hands and the suture, are cumbersome, thus impeding the surgeon's ability to appropriately place the suture knot.

In response to this problem, surgeons have sought alternatives to conventional knot-tying techniques. Various sutures and suture terminating devices have been disclosed. The most frequently disclosed among these alternatives is the use of surgical clips, which are designed to replace suture knots.

Examples of surgical clips to terminate sutures have been disclosed in a number of patents including U.S. Pat. Nos. 3,976,079; 5,282,832; 5,078,731; 5,474,572; 5,171,251; and 5,409,499. In general, these devices contain locking mechanisms which require the surgeon to deform the device on the suture's path and entrap the suture material in the clip. The suture is fixed in a single location and thus the necessity of tying a knot on the suture is avoided. These devices are problematic because they require actuation and, more importantly, pinpoint accuracy by the surgeon since they are not adjustable.

Still other configurations of surgical clips are disclosed in U.S. Pat. Nos. 5,078,731; 5,474,572; 5,171,251; and 5,409,499. These clips are also actuated by the surgeon's deformation of the device. The locking mechanisms in these devices are incorporated into the device's body. However, lateral access is required in order to actuate these clips. This cumbersome configuration makes them difficult, if not impossible, to incorporate into prosthetics. Further, these clips also lock the suture into a single position once actuated. This abridges the surgeon's ability to further adjust the tension on the suture, thus requiring the surgeon to remove the suture and repeat the process in order to achieve, when necessary, better coaptation of the tissue by the suture.

Still other surgical clips are disclosed in U.S. Pat. Nos. 3,976,079 and 5,282,832. Both of these clips incorporate an additional mating component (retaining clip 96 and retainer 120, respectively), which when attached to the clip locks the suture in place. However, the use of small loose parts is highly undesirable since it is easy to drop and lose such pieces through a minimally invasive incision. Indeed, if this were to occur, for example, inside a patient's heart, the potential for an arterial embolus and patient injury would greatly increase. Again, these clips, like all the aforementioned clips, lock the suture into a single position, which, as discussed above, has many disadvantages.

Additionally, modifications of sutures and surgical ties have been disclosed in U.S. Pat. Nos. 5,123,913 and 4,955,913. The methods presented in these patents include the use of a modified suture or surgical tie having serrations or ridges on the suture's or tie's bodice, which when mated with the appropriate closure device, the suture or tie is allowed to be freely advanced towards closure and cannot slide backwards. This allows the surgeon to incrementally increase the tension on the suture or tie without the need to tie a knot. These modified sutures/ties are not suitable for most surgical applications, since they can not be passed through tissue or prosthetics like a standard suture. In addition, neither of these devices afford the surgeon with the opportunity for precise tightening of the suture or tie since the serrations or ridges are incremental. Further, U.S. Pat. No. 5,123,913 discloses a modified suture terminating with a loop member which is designed to mate with the serrations along the length of the suture. While this will function as a surgical suture, the loop member increases the length of the device, making it unsuitable for certain surgical applications, such as securing a heart valve inside the heart. Additionally, these inventions are not compatible with standard sutures.

U.S. Pat. No. 5,776,188 discloses three pertinent apparatus for securing a suture without a knot to a heart valve sewing ring. In the first apparatus, plugs 192 (as illustrated in FIG. 5) have been credited as devices which help secure the suture in place. This is similar to the suture clip methodology which was discussed above. The drawbacks associated with these plugs are that they: (1) do not eliminate the need for a knot to be tied, (2) do not allow the tension to be incrementally adjusted on the suture, (3) have the potential to dislodge causing patient injury, and (4) may be difficult to position in a minimally invasive cardiac procedure.

The second apparatus provided by U.S. Pat. No. 5,776,188, incorporates the use of ball 248 and chamfered slot 242. As illustrated in FIG. 7, the ball and slot cooperate to effectuate the securing of sutures to a heart valve sewing ring without the necessity of a knot. While this embodiment may fasten a suture to the valve sewing ring, it is undesirable to surgeons for a number of reasons. First, this embodiment utilizes a free-floating piece (ball 248) which has the potential to dislodge or jam. Consistent with the concerns raised above, relating to U.S. Pat. Nos. 3,976,079 and 5,282,832, if the ball were to dislodge from the device, it could harm the patient. Further, although this embodiment may engage the suture, the rounded nature of the ball will minimize the field of contact and the resulting integrity of the grip thereon. This greatly reduces suitability for such a device since most surgical procedures require a strong and permanent grip.

The final apparatus disclosed within U.S. Pat. No. 5,776,188 relies on pressure generated by spring 252 to secure the suture. More particularly, spring 252, which is a small separate piece attached to the device, impedes the sutures movement by trapping it. Therefore, the stronger the spring used, the more pressure it applies to the suture and the more reliable its grip will be. However, as the pressure increases, the surgeon's ability to adjust or fine tune the tension applied to the suture is hampered. In addition, the strength of the grip is directly dependent upon the spring's stamina and strength. Further, consistent with the above discussion relating to the previous apparatus, spring 252 is not captured within the body of the device; accordingly, it is capable of breaking free from the device which could cause patient injury.

As will be more fully appreciated below, none of the aforementioned devices offer the ease and versatility for terminating sutures and thus securely locking tissues and/or prosthetics in place, as the instant invention. Indeed, the instant invention provides a means for securing tissues to native tissues and prosthetic implants to native tissue; the benefits of which may be most appreciated in operations where minimally invasive procedures are utilized.

The apparatus and systems disclosed herein obviate the need for manually tying knots, a procedure which typically requires the surgeon to manipulate his hands in tight proximity of the tissue being secured. This invention may be used as a freestanding device or may be incorporated into prosthetic implants such as heart valves, annuloplasty rings, orthopedic implants or the like, all of which require securing to native tissues.

Moreover, the devices of the instant invention are applicable to all instances of operative procedures where the surgeon needs to secure tissue with a suture, but has limited access for her/his hands to tie a knot. In instances of using sutures to stop bleeding or securing tissues or implants in mi ally invasive procedures, the devices of the instant invention will facilitate the procedure by eliminating the time and physical exposure required to manually tie knots to terminate the suture. The present invention's advantages of enhanced tissue securing with minimal surgical exposure, decreased implementation time, and enhanced reliability are accentuated when compared to existing related technology.

SUMMARY OF THE INVENTION

The present invention is directed to apparatus and systems for use in securing the ends of sutures. This invention can be used in a freestanding manner to terminate a suture which holds tissue together or it can be incorporated into a prosthetic in order to hold tissue to the prosthetic. The present invention terminates the ends of standard sutures without knots and without the need for manual proximity thus facilitating minimally invasive surgical procedures.

In one embodiment, the instant invention provides a suture securing apparatus comprising: an apparatus body having a upper surface, a lower surface, an outer surface, and at least one aperture, the aperture having a longitudinal axis extending from the upper surface to the lower surface and defining an aperture surface, wherein a first longitudinal direction and a second longitudinal direction thereof each extends along the longitudinal axis in opposite dictions, the aperture including an integral locking means for engaging a suture threaded therethrough.

In a preferred embodiment of the instant invention, the locking means of the suturing securing apparatus comprises a least one ridge formed on at least a portion of the aperture surface for engaging the suture threaded therethrough, each ridge so formed as to facilitate the movement of a suture in the first longitudinal direction along the aperture and oppose the movement of the suture in the second longitudinal direction along the aperture. In another preferred embodiment of the invention, the locking means of the suture securing apparatus comprises a plurality of ridges formed on at least a portion of the aperture surface for engaging the suture threaded therethrough, each ridge so formed as to facilitate the movement of a suture in the first longitudinal direction along the aperture and oppose the movement of the suture in the second longitudinal direction along the aperture. In other preferred embodiments of the invention, each ridge is formed from an elastic material or a rigid material. In yet another preferred embodiment of the invention, a portion of each ridge extending farthest from the aperture surface is rounded. In a preferred embodiment of the invention, each ridge is formed at an angle of greater than about 30° to the longitudinal axis of the aperture and, even more preferably, each ridge is formed at an angle of about 45° to the longitudinal axis of the aperture.

In a preferred embodiment of the instant invention, the apparatus body of the suture securing device comprises a first aperture and a second aperture, wherein each ridge formed on the first aperture surface is so formed as to facilitate the movement of a suture in the first longitudinal direction along the first aperture and oppose the movement of the suture in the second longitudinal direction along the first aperture and wherein each ridge formed on the second aperture surface is so formed as to facilitate the movement of a suture in the first longitudinal direction along the second aperture and oppose the movement of the suture in the second longitudinal direction along the second aperture, wherein the first longitudinal direction along the first aperture and the first longitudinal direction along the second aperture are directed to the upper surface of the apparatus body. In another preferred embodiment of the instant invention, the first and second apertures are mirror images of each other, as defined by a mirror plane equidistant from them.

In a preferred embodiment of the instant invention, the apparatus body comprises a first aperture and a second aperture, wherein each ridge formed on the first aperture surface is so formed as to facilitate the movement of a suture in the first longitudinal direction along the first aperture and oppose the movement of the suture in the second longitudinal direction along the first aperture and wherein each ridge formed on the second aperture surface is so formed as to facilitate the movement of a suture in the first longitudinal direction along the second aperture and oppose the movement of the suture in the second longitudinal direction along the second aperture, wherein the first longitudinal direction along the first aperture and the second longitudinal direction along the second aperture are directed to the upper surface of the apparatus body. In other preferred embodiments of the instant invention, the suture securing apparatus is made from biocompatible materials or biodegradable materials.

In a second embodiment, the instant invention provides a suture securing apparatus comprising: (a) an apparatus body having a upper surface, a lower surface, an outer surface, and at least one aperture, the aperture having a longitudinal axis extending from the upper surface to the lower surface and defining an aperture surface, wherein a first longitudinal direction and a second longitudinal direction thereof each extends along the longitudinal axis in opposite directions, the aperture consisting of an upper portion, a middle portion, and a lower portion, the upper portion bounded by the upper surface of the apparatus body and the middle portion, the middle portion bounded by the upper portion and the lower portion, and the lower portion bounded by the middle portion and the lower surface of the apparatus body, wherein the middle portion has a first surface and second surface opposing each other and is wider than either of the upper portion and the lower portion and forms a cavity therein; and (b) a movable cam member disposed in the middle portion of the aperture, the cam member having an engagement end and a rotation end, the rotation end being wider than the width of the upper portion of the aperture thereof and the width of the lower portion of the aperture thereof and disposed near the second surface, and the engagement end disposed near the first surface; wherein the cam member moves to an unengaged position to facilitate the movement of a suture threaded through the aperture in the first longitudinal direction along the aperture and moves to an engaged position to engage the suture threaded through the aperture in the second longitudinal direction by compressing the suture between the engagement end of the cam member and the first surface of the middle aperture to oppose the movement of the suture in the second longitudinal direction along the aperture.

In a preferred embodiment of the instant invention, the first surface of the middle aperture comprises at least one ridge, each ridge so formed as to facilitate the movement of a suture in the first longitudinal direction along the aperture and oppose the movement of the suture in the second longitudinal direction along the aperture. In another preferred embodiment of the instant invention, the first surface of the middle aperture comprises a plurality of ridges, each ridge so formed as to facilitate the movement of a suture in the first longitudinal direction along the aperture and oppose the movement of the suture in the second longitudinal direction along the aperture. In yet other preferred embodiments of the instant invention, each ridge is formed from an elastic material or a rigid material.

In yet another preferred embodiment of the instant invention, the engagement end of the cam member comprises serrations to grip the suture when engaged. In another preferred embodiment of the instant invention, the apparatus body includes a first aperture with a first movable cam member therein and a second aperture with a second movable cam member therein, wherein the first movable cam member moves to an unengaged position to facilitate the movement of a suture threaded through the first aperture in the first longitudinal direction along the aperture and moves to an engaged position to engage the suture threaded through the first aperture in the second longitudinal direction by compressing the suture between the engagement end of the first movable cam member and the first surface of the middle aperture thereof to oppose the movement of the suture in a second longitudinal direction along the first aperture; wherein the second movable cam member moves to an unengaged position to facilitate the movement of a suture threaded through the second aperture in the first longitudinal direction along the second aperture and moves to an engaged position to engage the suture threaded through the second aperture in the second longitudinal direction by compressing the suture between the engagement end of the first movable cam member and the first surface of the middle aperture thereof to oppose the movement of the suture in a second longitudinal direction along the second aperture; and wherein the first longitudinal direction along the first aperture and the first longitudinal direction along the second aperture are both directed to the upper surface of the apparatus body. In yet another preferred embodiment of the instant invention, the first and second apertures and first and second cam members are mirror images of each other, as defined by a mirror plane equidistant from them.

In still another preferred embodiment of the instant invention, the apparatus body includes a first aperture with a first movable cam member therein and a second aperture with a second movable cam member therein, wherein the first movable cam member moves to an unengaged position to facilitate the movement of a suture threaded through the first aperture in the first longitudinal direction along the aperture and moves to an engaged position to engage the suture threaded through the first aperture in the second longitudinal direction by compressing the suture between the engagement end of the first movable cam member and the first surface of the middle aperture thereof to oppose the movement of the suture in a second longitudinal direction along the first aperture; wherein the second movable cam member moves to an unengaged position to facilitate the movement of a suture threaded through the second aperture in the first longitudinal direction along the second aperture and moves to an engaged position to engage the suture threaded through the second aperture in the second longitudinal direction by compressing the suture between the engagement end of the first movable cam member and the first surface of the middle aperture thereof to oppose the movement of the suture in a second longitudinal direction along the second aperture; and wherein the first longitudinal direction along the first aperture and the second longitudinal direction along the second aperture are both directed to the upper surface of the apparatus body. In other preferred embodiments of the instant invention, the suture securing apparatus is made from biocompatible materials or biodegradable materials.

The instant invention also contemplates securable medical prosthesis device comprising a medical prosthesis device in physical contact, physical engagement, or integrally formed with at least one suture securing apparatus according to the instant invention. Such medical prosthesis devices include a sewing ring implant shaped and sized for attachment to the inner surface of a native annulus, the sewing ring implant having a plurality of suture securing apparatuses distributed around the circumference of the sewing ring implant.

DESCRIPTION OF THE PREFERRED EMBODIMENTS

Figure 1:
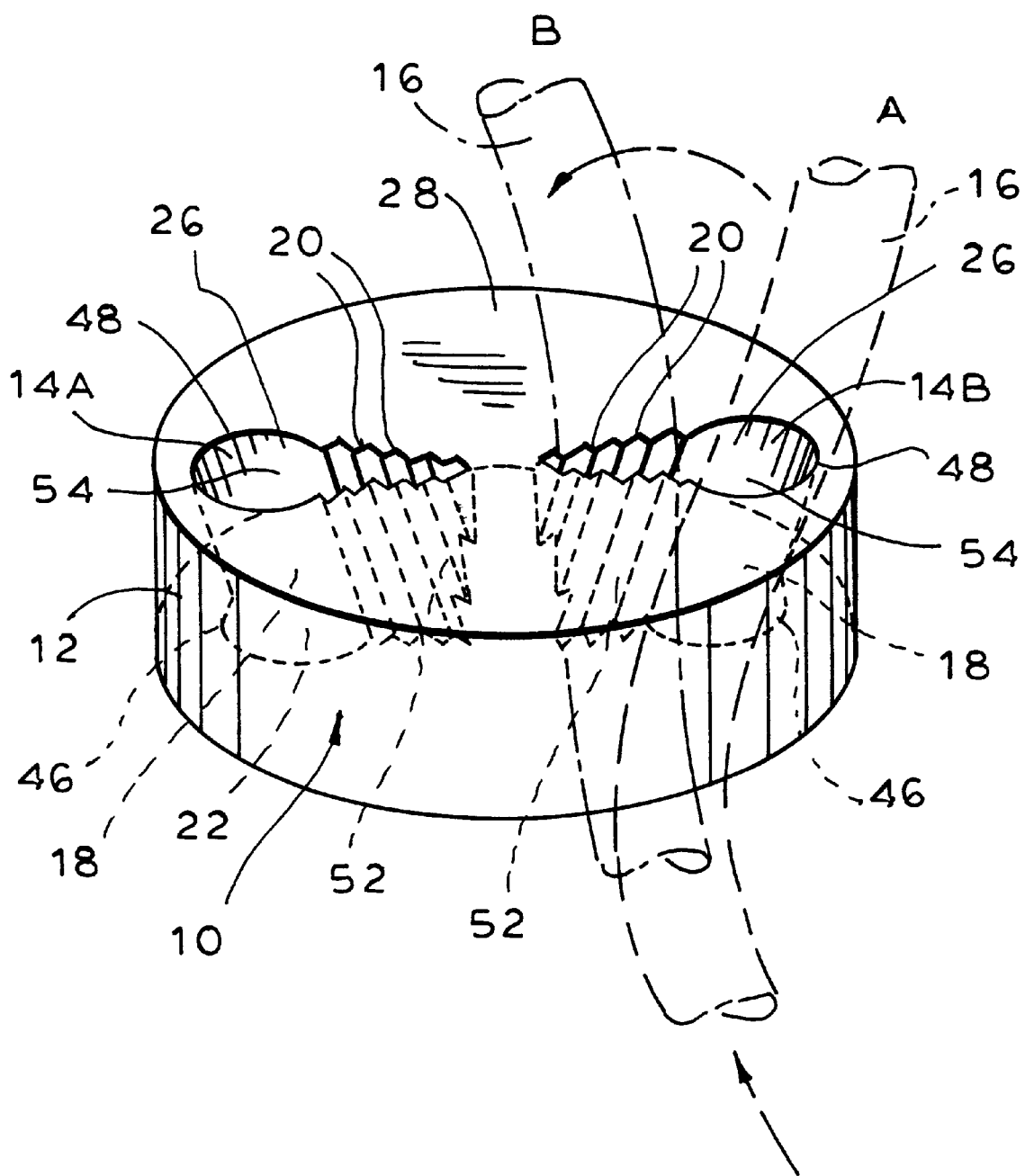
FIG. 1 is a top perspective view of a freestanding suture terminating device showing a technique for terminating a suture in accordance with one embodiment of the present embodiment.
Figure 2:
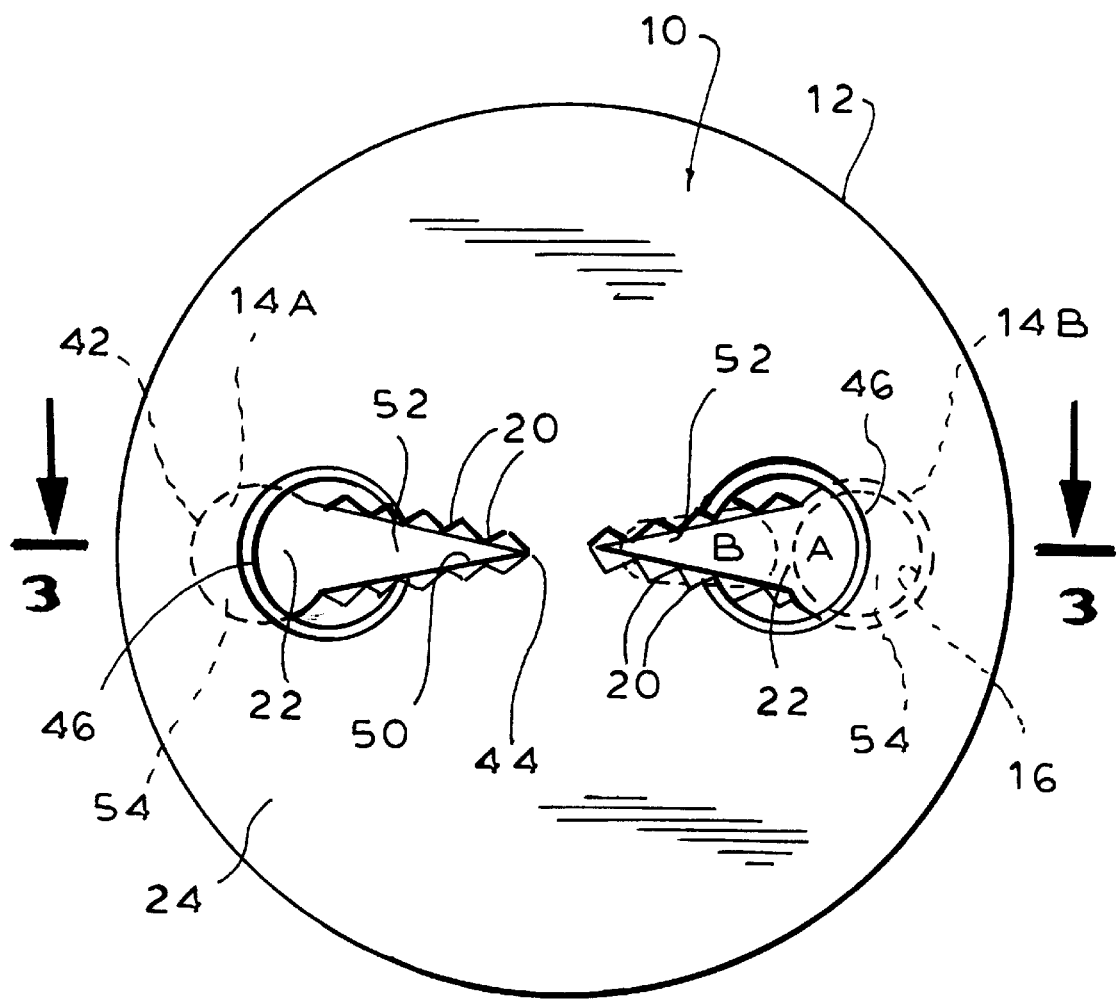
FIG. 2 is a top plan view of the suture terminating device of FIG. 1.
Figure 3:
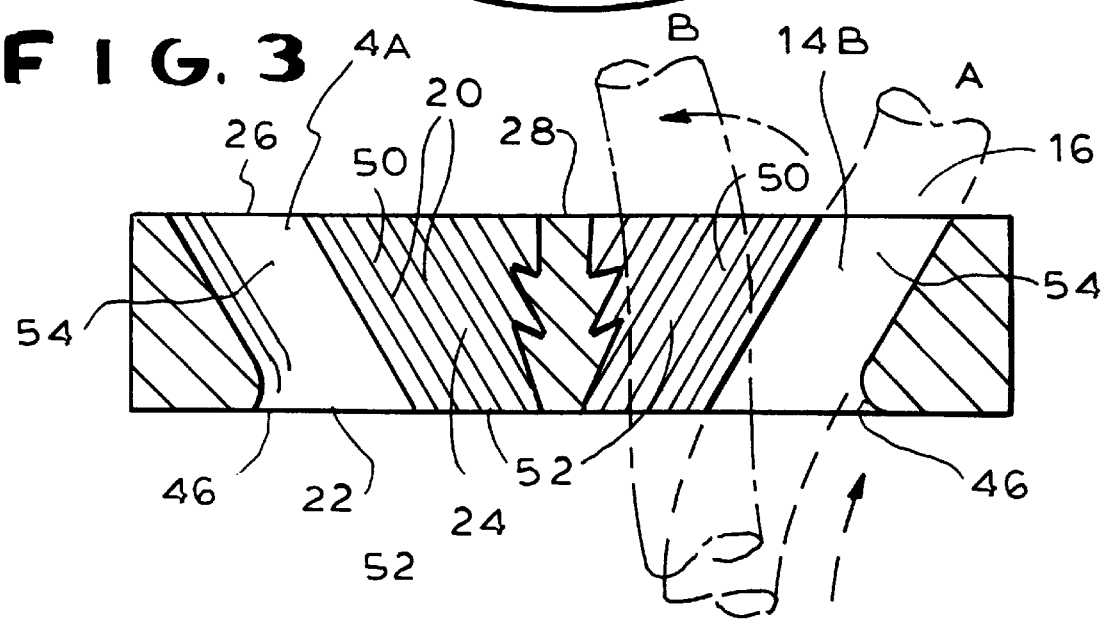
FIG. 3 is a cross-sectional view of a suture terminating device taken along line 2—2 of FIG. 2 showing a technique for terminating a suture in accordance with one embodiment of the present embodiment.

FIGS. 1–3 illustrate a freestanding version of the instant suture terminating device 10 in accordance with one embodiment of the present invention. As depicted, the present suture terminating device consists of a main member 12 having apertures 14(a) and 14(b) positioned therein to facilitate the threading of standard suture 16 therethrough. As the surgeon draws suture 16 through aperture 14, suture 16 is secured in place by the locking mechanism 18 which is housed within that same aperture 14.

Figure 4:
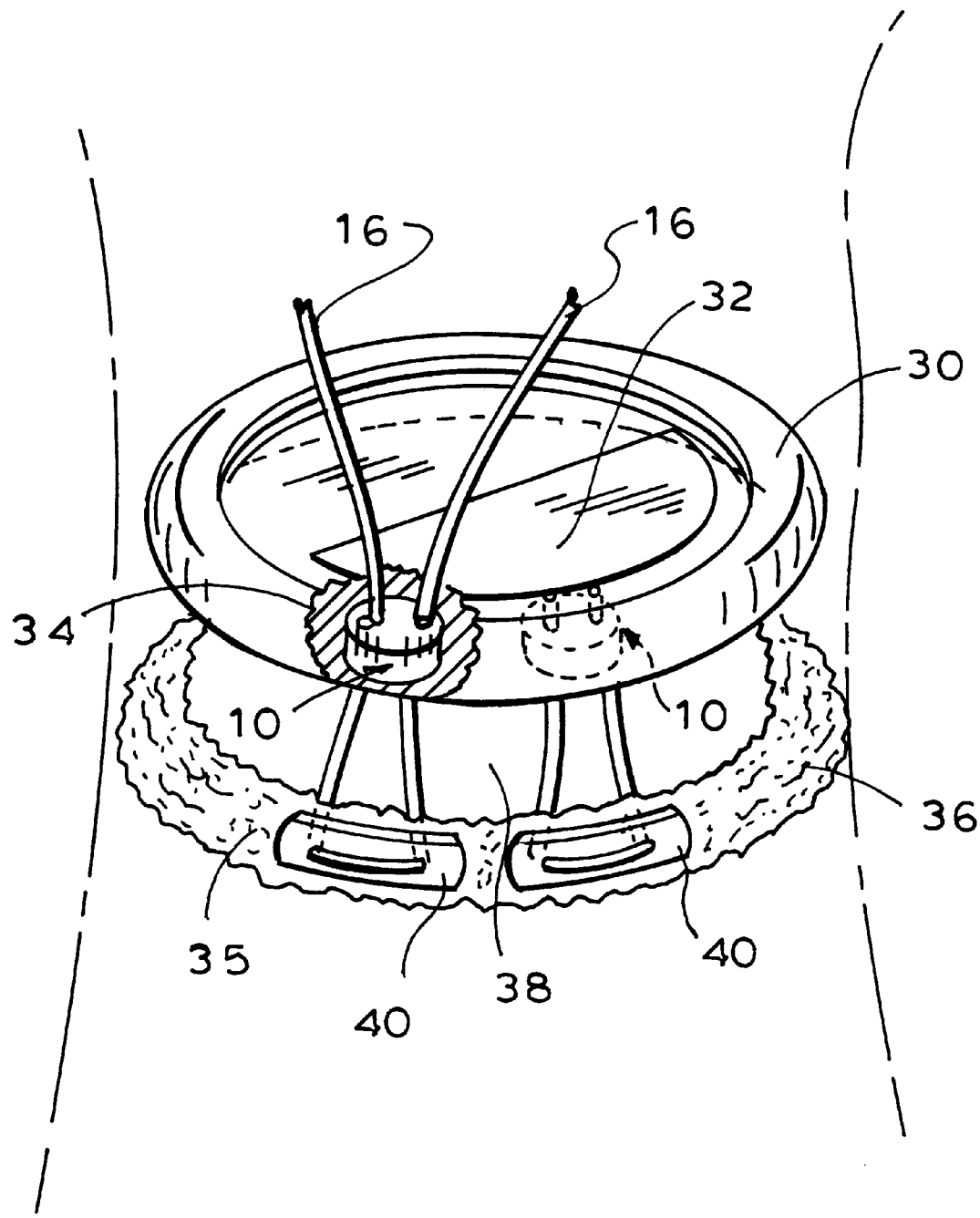
FIG. 4 is a top perspective partially exploded view of an artificial arterial valve attached to the native tissue of the aorta in accordance with the present invention cut-away to reveal a suture terminating device, in accordance with the present invention, incorporated therein.

Main member 12, which may (as illustrated in FIG. 1) exist as a freestanding device or (as illustrated in FIG. 4) be incorporated into a prosthetic device, may be constructed in a variety of manners including the milling or molding of biocompatible plastics and metals, or biodegradable materials. Depending upon the device's actual application, the size of the suture, and the material used, main member 12 should be large enough to both contain and support the sutures drawn therethrough without disruption or distortion to the local native tissue and/or the prosthetic device attached thereto or thereby. For example, if main member 12 is constructed of stainless steel and is intended to be used with 2-0 braided synthetic suture material for securing a heart valve sewing ring, then the main member 12 should be 0.1" (width) by 0.15" (length) by 0.1" (thickness). The width of main member 12 must naturally be greater than the diameter of the suture 16 which it is intended to contain and terminate.

An additional benefit of the present embodiment is that, under certain circumstances, main member 12 also functions as a pledget (i.e., dispersing the pressure of the suture over a surface area greater than that of the suture alone, thus bolstering the suture's coupling of the desired members (i.e., tissue to native tissue and/or prosthetic to native tissue) while reducing the likelihood of damage to the prosthetic device or the surrounding tissue.

The present suture terminating device will preferably incorporate two apertures within the main member 12 of the device. Apertures 14(a) and 14(b) are generally housed in the midline of main member 12. Although the apertures' alignment may vary under certain circumstances, they will generally have, as illustrated in FIG. 2, a mirror image orientation to one another. When arranged in this configuration, the apertures cooperate as pairs, each member receiving one of the two ends of the suture being secured. Each aperture, whether functioning independently or as a member of a cooperating pair, comprises a first opening 22 in the bottom portion 24 of main member 12, a locking mechanism 18, and a second opening 26 in the top portion 28 of main member 12.

First opening 22 is round in nature and of adequate size to accommodate the berth of suture 16. Further, as illustrated in FIG. 3, first opening 22 may be accentuated in a conical fashion in order to facilitate the surgeon's threading of suture 16 therethrough. Second opening 26 is eccentric and bi-polar. Returning to FIG. 2, first pole 42 is generally round with sufficient diameter to accommodate the berth of suture 16. Second pole 44 is formed by an acute angular narrowing orientated towards the axis of second opening 26. The rounded portions 46 and 48 of the first and second openings 22 and 26, respectively, are preferably offset from each other.

FIG. 3 depicts an alternate rendition of the present embodiment in which the inner surface 50 of the angulated portion 52 of aperture 14 may be lined with ridges 20, although under certain circumstances a single ridge may suffice. Ridges 20 are preferably shaped and oriented so as to facilitate the passage of the suture in one direction and to oppose any movement in the other. The number, density, and amplitude of the ridges should be increased as the overall dimensions of the device and suture material used increases. The apex of the ridges are preferably rounded; this facilitates the entry of the suture material into the locking mechanism, while avoiding the use of a sharp edge which could potentially abrade, damage, or weaken the suture. Although it is generally preferable for the ridges to be constructed in an unyielding or rigid form, it may be desirable in certain circumstances to construct the ridges such that they possess elastic qualities in order to further enhance their gripping action. The longitudinal axis of ridges 20 generally extend out from the inner surface 50 of the angulated portion 52 at a 45° angle. The total taper (from bottom to top) between the opposing segments of aperture 14 which form the angulated portion 52 is, in the present version of this embodiment, 4°.

The apertures' orientation insures that when upward tension is placed on the suture, the suture is coerced, as illustrated in FIGS. 1–3, from position A in the rounded portion of 54 into angulated portion 52 of aperture 14, where the locking mechanism engages the suture, thus locking it in place. In other words, once the surgeon has positioned the tissue or prosthetic device, the suture terminating device need only be held in place while tension is applied simultaneously to both ends of the suture. This transverses and engages the locking mechanism within the aperture. As tension is placed on the suture and it is drawn through the aperture, the ridges lining the aperture engage the suture in a manner ensuring that the suture may advance, but not regress through the aperture. Multiple points of contact are made between the ridges lining the aperture and the suture material, thus providing for a secured union. Back pressure on the suture from the native tissue maintains its fixation within the suture terminating device's locking mechanism.

Generally, the suture is drawn through the device by the surgeon into its final position, thus providing the desired tension and coaptation of tissue by the suture. However, should the surgeon need to loosen the suture (in order to reposition it for example), the free ends of the suture could be pulled away from the narrowed angulated portion of the apertures. This maneuver would disengage the locking mechanism. Once disengaged, the suture is free to move in rounded portion 54 of aperture 14. In order to resecure the suture, the surgeon would again place tension on the suture to engage it in the locking mechanism and advance the suture until the desired tension was achieved.

FIG. 4 displays still another embodiment of the present invention. More particularly, as the cutaway view of FIG. 4 depicts, suture terminating device 10 is positioned inside valve 30 in this embodiment. Consistent with standard suturing techniques, suture 16 enters valve 30 from its bottom, is threaded through the suture terminating device positioned therein, and exits from the valve's top.

Under certain circumstances, it may be desirable for the surgeon to use a pledget when securing a suture with the suture terminating device of the present invention. For instance, when the portion of the suture terminating device contacting the tissue and/or the prosthetic is too small to effectively disperse the pressure placed upon that same tissue and/or prosthetic secured by the suture or suture terminating device, then the use of a pledget is desirable.

As discussed above, the use of a pledget may also be desirable when used in conjunction with the securing of a prosthetic to native tissue. For example, if suture terminating device 10 were incorporated in artificial arterial valve 30, as illustrated in FIG. 4, were constructed of stainless steel and were intended to be used with 2-0 braided synthetic suture material for securing the sewing ring of an artificial arterial valve, then it might be desirable for the surgeon to use pledgets 40 in order to reduce the risk of damage to the valve 30 or the surrounding tissue (aorta wall 36 in this case). Although pledgets may take many forms, they are generally manufactured from TEFLON® or DACRON®. They function by increasing the surface area over which the suture's tension is distributed.

Although placement of the pledget may vary from procedure-to-procedure, generally the surgeon, as illustrated in FIG. 4, will thread suture 16 first through pledget 40, then through the native tissue (aorta wall 36 in this case), and ultimately through the prosthetic and the suture terminating device 10 implanted therein. As depicted in the present illustration, the suture 16 transverses through valve 30 thus securing artificial arterial valve 30 to aorta 35. Once in place, the surgeon engages the locking mechanism as discussed above, and if satisfied with the coaptation, cuts off and removes the excess suture material.

A second preferred embodiment of the present invention is depicted in FIGS. 5–8. In this embodiment, suture terminating device 70 consists of a main member 72 having apertures 74(*a*) and 74(*b*) positioned therein to facilitate the threading of standard sutures 76 therethrough. As the surgeon draws the suture 76 through aperture 74, the suture is secured in place by locking mechanism 78 which is housed within the aperture.

Suture terminating device 70 may be constructed in a variety of manners including the milling or molding of biocompatable plastics and metals, or biodegradable materials. Depending upon the actual application, the size of the suture, and the material used, main member 72 should be large enough to both contain and support the sutures drawn therethrough without disruption or distortion to the local native tissue and/or the prosthetic device attached thereto or thereby.

Figure 5:
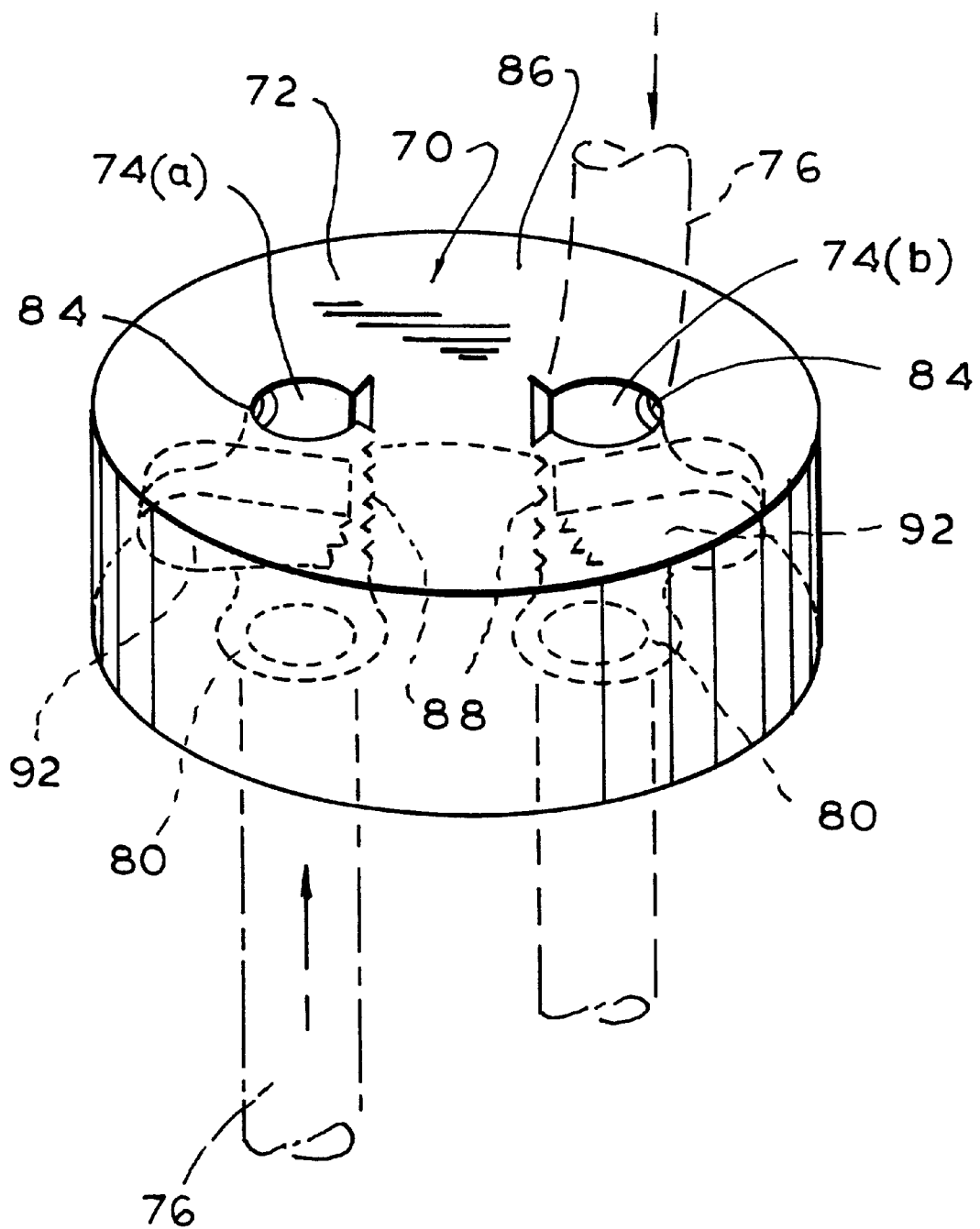
FIG. 5 is a top perspective view of a freestanding suture terminating device showing a technique for terminating a suture in accordance with another embodiment of the present embodiment.

As depicted by FIG. 5, apertures 74(*a*) and 74(*b*) which are housed within main member 72 comprise a fist opening 80 in the bottom portion 82 of main member 72, a locking mechanism 78, and a second opening 84 on the top portion 86 of the main member. The first opening 80 is somewhat conical in nature, to facilitate the surgeon's introduction of the suture into the aperture. The second opening 84 is preferably round in nature and adequately sized to accommodate the berth of suture 76. Preferably, first and second openings 80 and 84 are aligned on top of each other. The orientation of aperture 74, is normal to that of main member 72.

Figure 6:
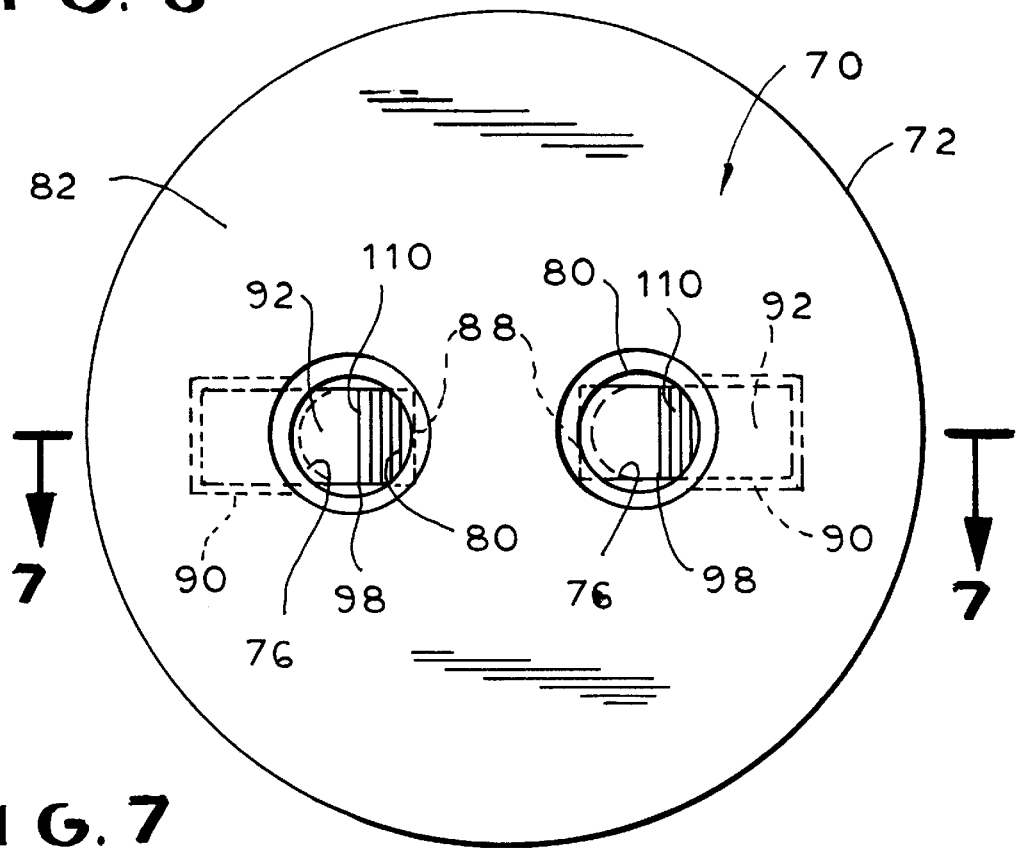
FIG. 6 is a bottom plan view of the suture terminating device of FIG. 5.

The version of the present embodiment of the suture terminating device illustrated in FIGS. 5–8 incorporates two apertures within the main member 72 of the device. Apertures 74(*a*) and 74(*b*) are generally housed in the midline of main member 72. Although the placement of the apertures within suture terminating device 70 may vary under certain circumstances, they will generally have, as illustrated in FIG. 6, a mirror image orientation to one another. When arranged in this configuration, the apertures cooperate as pairs, each member receiving one of the two ends of the suture being secured. Each aperture, whether functioning independently or as a member of a cooperating pair, comprises, as discussed above and as illustrated by FIG. 7, a first opening 80 in the bottom portion 82 of main member 72, a locking mechanism 78, and a second opening 84 in the top portion 86 of main member 72.

Figure 7:
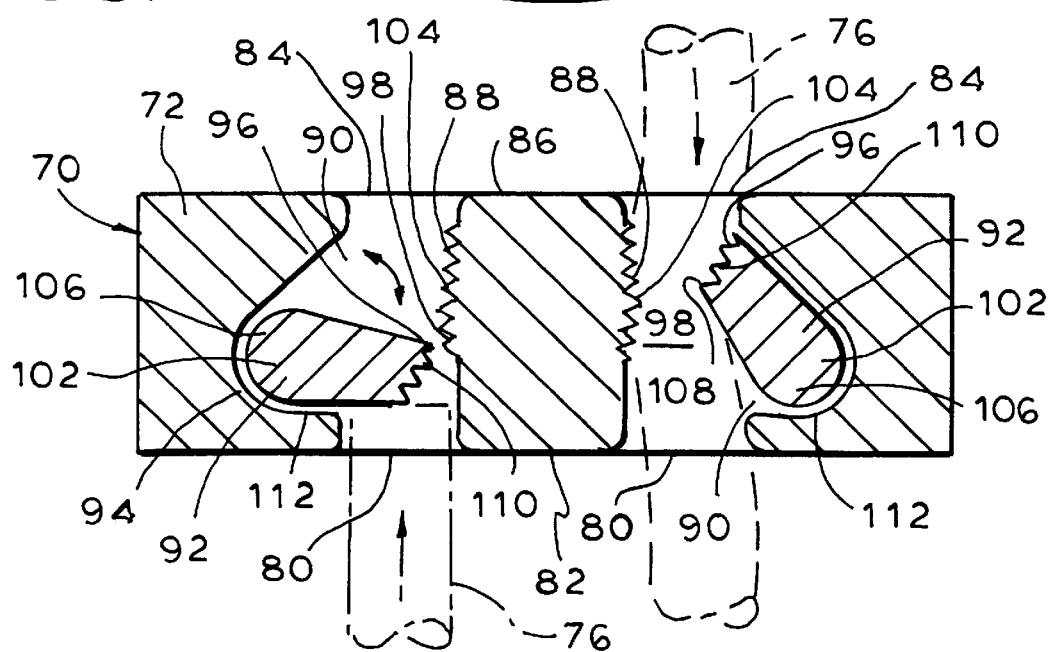
FIG. 7 is a cross-sectional view of a suture terminating device taken along line 7—7 of FIG. 6 showing a technique for terminating a suture in accordance with another embodiment of the present embodiment.
Figure 8:
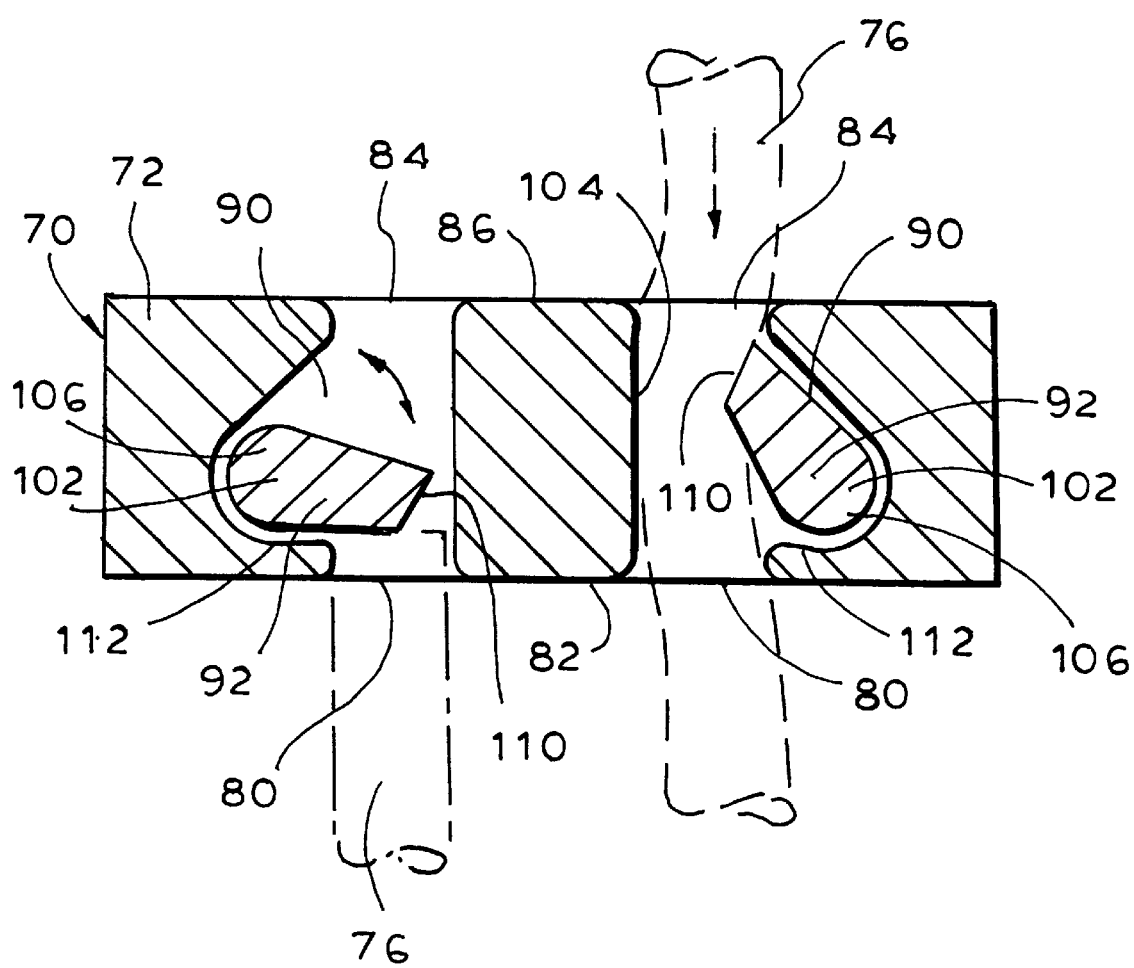
FIG. 8 is a cross-sectional view of a suture terminating device also taken along line 7—7 of FIG. 6 showing a technique for terminating a suture in accordance with still another embodiment of the present embodiment.

As depicted in FIG. 7, medial aspect 104 of aperture 74 is flat, and is preferably lined with ridges or serrations 88 which are generally perpendicular to the aperture's orientation. Although, as depicted with FIG. 8, the ridges or serrations 88 may be absent in certain applications. Extending from aperture 74 and vertically aligned with directly medial aspect 104 within main member 72 is cavity 90, which has a rounded portion 98 preferably formed at the point furthest from the medial aspect of aperture 74.

Housed within cavity 90 is cam member 92. The thickness of cam member 92 would typically be uniform. It is preferably narrower than the diameter of aperture 74 and cavity 90. Cam member 92 is eccentric, having a swollen rounded portion 94 at the first end 106, and a protuberance 96 extending out from second end 108.

The rounded portion 94 of cam member 92 cooperates with the rounded portion 98 of cavity 90. To ensure that cam member 92 is permitted to move radially in a north/south orientation within cavity 90.

Cam member 92 is captured within cavity 90, since the largest dimension of the cam member is larger than either end opening of the aperture. This capturing prevents cam member 92 from breaking free from suture terminating device 70 and causing injury to the patient. Further, the spatial relationship between cam member 92 and cavity 90 minimizes any potential for mechanical failure associated with terminating device 70.

The second end 108 of cam member 92 protrudes into the center lumen of aperture 74. Preferably, there are ridges 110 on the surface of the second end of cam member 92. These ridges are, most preferably, orientated to cooperate with the ridges 88 on medial aspect 100 of aperture 74.

Cam member 92 and its mating receptacle in the wall of the aperture 74 are eccentric such that when cam member 92 is rotated in an upward direction, the eccentric edge of cam member 92 moves away from center lumen of the aperture rotating into the receptacle. When cam member 92 is rotated downwards, the cam member edge is brought further out into the lumen of the aperture and into incrementally increasing contact with the ridges lining the flat surface of the aperture apposition against the far wall of aperture 74. Engagement of locking mechanism 78 is accomplished when suture 76 is trapped between ridges 88 which medial aspect 100 of aperture 74 and ridges 110 which, as discussed above, line second end 78 of cam member 92. More precisely, as suture 76 is advanced through aperture 74, cam member 92 rotates, as illustrated by the arrows in FIG. 7 away from the medial aspect of aperture 74. Once the surgeon has applied her final tension to suture 76, back pressure from the native tissue causes suture 76 to slightly withdraw from aperture 74. As suture 76 withdraw, ridges 110 on cam 92 frictionally engages suture 76. This, in turn, causes cam 92 to rotate radially with suture 76. The asymmetric shape of cam member 92 ensures that, as cam member 92 rotates, ridges 110 cooperate with ridges 88 on the medial aspect of aperture 74, thus trapping the suture therein. Over rotation, which would undermine the integrity of locking mechanism 78, is prevented by retaining wall 112 of cavity 90.

If the surgeon needs to readjust the suture, placing tension on the suture end it will pull it upwards and disengage the second member from its trapped position against the aperture wall. Once repositioned, tension is reapplied, the second member re-engaged, and the suture locked into place.

EXAMPLE 1

By way of example, this invention may be incorporated, as provided above, into heart valve prosthetics. By incorporating the present invention into the sewing ring of a heart valve or heart annuloplasty ring or device, the surgeon would merely have to feed the sutures into appropriately located apertures. The prosthesis would be positioned, and the sutures locked into place without the need for the proximity of manual knot tying.

Typically the surgeon would place double ended sutures through the native annular tissue in a concentric fashion around the valve annulus. Each paired suture end would then be threaded through the appropriately paired knotless suture device. These devices will be incorporated into the perimeter of prosthetic valve sewing ring at appropriate distances depending upon the application. The valve is then advanced from outside the patient's body into the heart. The surgeon then removes all slack from the suture the valve would then be placed in its desired position. Once engaged, the back pressure of the native tissue ensures that the suture remains locked within the suture terminating device. Depending upon the type of suture used (and the elasticity associated with the same), contraction of the suture may also compliment the engagement of the locking mechanism.

After verification of proper tension and valve position, the suture ends are cut off. This is particularly advantageous for use with minimally invasive techniques since, as discussed above, these apparatus and systems obviate the need for tying knots.

EXAMPLE 2

The present invention will also be useful for thorascopic thoracic surgery. It is necessary to place sutures to stop bleeding during thoracic surgery. This invention would allow standard suture technique to be use through thorascopic ports, without forcing proximity to the site of the suture in order to terminate the suture ends. In this application, the body of the device (with two apertures) could either be used alone to terminate a suture or the device could be utilized with a pledget. In this fashion, once a standard suture is placed into the bleeding tissue, tension is placed on the tissue to compress and stop the bleeding. Normally the surgeon would then tie a knot to terminate the suture with the proper tension. Instead, using the suture securing device of the instant invention, the present suture termination is advanced along the suture until it encounters the tissue to be ligated. Tension is applied to the sutures. Once the desired tension on the ligated tissue is achieved, the suture terminating device is engaged, and the excess suture is trimmed.

If the tissue compression is required to be distributed over a greater surface area than that provided by the bottom of the body of the current invention or of a pledget, then the present suture terminating device should be incorporated into a fabric cuff which will enlarge the contact area.

EXAMPLE 3

Likewise, the suture securing device of the instant invention can be used in orthopedic surgery to terminate sutures which are placed arthroscopically, where access for manual knot tying is limited. In this application, sutures are placed in standard fashion to repair torn ligaments. The knotless suture device of the instant invention would be threaded over the suture ends and advanced to the site of the repair. After the final appropriate tension had been applied to the suture material, the locking mechanism is engaged. Subsequently, the suture ends are cut off.

For the reasons discussed throughout, this application is highly desirable since it would avoid the necessity of manual proximity to tie a knot. Additionally, the embodiments of this invention can be incorporated into orthopedic implants to enhance and facilitate their fixation to native tissue.

As is known in the art, all exposed parts of the invention should generally be made of biocompatible materials, either synthetic or natural, from which surgical implants are typically made, for example, polymers, plastics, biological tissue, metals and alloys, and combinations thereof. In addition, embodiments of this invention can be constructed of biodegradable materials.

As noted above, the Figures and Examples provided are intended to further describe the aspects of the present invention. Thus, the Figures and Examples are illustrative only and are not to be construed as limiting the scope of that which is regarded as the invention. Furthermore, while only two embodiments of the invention has been presented in detail in this disclosure, it will be apparent to those of skill in the art that many modifications, adaptations, and changes may be made thereto without departing from the spirit and scope of the invention. In short, the scope of the present invention is only to be limited by the following claims and the equivalents thereto.

What is claimed is:

1. A suture securing apparatus comprising:
    an apparatus body having an upper surface, a lower surface, a first internal surface, a second internal surface, an outer surface, and at least one aperture,
    the aperture having a longitudinal axis extending from the upper surface to the lower surface, a latitudinal axis extending from the first internal surface to the second internal surface, and defining an aperture surface, wherein a first longitudinal direction and a second longitudinal direction thereof each extends along the longitudinal axis in opposite directions, and a first latitudinal direction and a second latitudinal direction thereof each extends along latitudinal axis in opposite directions, the aperture including an integral locking means for engaging, and disengaging from, a suture threaded therethrough,
    the locking means formed so as to facilitate the movement of a suture in the first longitudinal direction and the first latitudinal direction along the aperture and to oppose the movement of the suture in the second longitudinal direction along the aperture until pressure is applied to the suture in the second latitudinal direction, thereby disengaging the locking means and permitting the movement of the suture in the second longitudinal direction along the aperture.

2. The suture securing apparatus according to claim 1, wherein the locking means comprises at least one ridge formed on at least a portion of the aperture surface for engaging, and disengaging from, the suture threaded therethrough, each ridge so formed as to facilitate the movement of a suture in the first longitudinal direction and the first latitudinal direction along the aperture and oppose the movement of the suture in the second longitudinal direction along the aperture until pressure is applied to the suture in the second latitudinal direction, thereby disengaging the locking means and permitting the movement of the suture in the second longitudinal direction along the aperture.

3. The suture securing apparatus according to claim 2, wherein the locking means comprises a plurality of ridges formed on at least a portion of the aperture surface for engaging, and disengaging from, the suture threaded therethrough, each ridge so formed as to facilitate the movement of a suture in the first longitudinal direction and the first latitudinal direction along the aperture and oppose the movement of the suture in the second longitudinal direction along the aperture until pressure is applied to the suture in the second latitudinal direction, thereby disengaging the locking means and permitting the movement of the suture in the second longitudinal direction along the aperture.

4. The suture securing apparatus according to claim 2, wherein each ridge is formed from an elastic material.

5. The suture securing apparatus according to claim 2, wherein each ridge is formed from a rigid material.

6. The suture securing apparatus according to claim 2, wherein the portion of each ridge extending farthest from the aperture surface is rounded.

7. The suture securing apparatus according to claim 2, wherein each ridge is formed at an angle of greater than about 30° to the longitudinal axis of the aperture.

8. The suture securing apparatus according to claim 7, wherein each ridge is formed at an angle of about 45° to the longitudinal axis of the aperture.

9. The suture securing apparatus according to claim 2, the apparatus body comprising a first aperture and a second aperture, wherein each ridge formed on the first aperture surface is so formed as to facilitate the movement of a suture in the first longitudinal direction and the first latitudinal direction along the first aperture and oppose the movement of the suture in the second longitudinal direction along the first aperture until pressure is applied to the suture in the second latitudinal direction, thereby disengaging the locking means and permitting movement of the suture in the second longitudinal direction along the aperture, and wherein each ridge formed on the second aperture surface is so formed as to facilitate the movement of a suture in the first longitudinal direction and the first latitudinal direction along the second aperture and oppose the movement of the suture in the second longitudinal direction along the second aperture until pressure is applied to the suture in the second latitudinal direction, thereby disengaging the locking means and permitting the movement of the suture in the second longitudinal direction along the second aperture, wherein the first longitudinal direction along the first aperture and the first longitudinal direction along the second aperture are directed to the upper surface of the apparatus body.

10. The suture securing apparatus according to claim 9, wherein the first and second apertures are mirror images of each other, as defined by a mirror plane equidistant from them.

11. The suture securing apparatus according to claim 2, the apparatus body comprising a first aperture and a second aperture, wherein each ridge formed on the first aperture surface is so formed as to facilitate the movement of a suture in the first longitudinal direction and the first latitudinal direction along the first aperture and oppose the movement of the suture in the second longitudinal direction along the first aperture until pressure is applied to the suture in the second latitudinal direction, thereby disengaging the locking means and permitting the movement of the suture in the second longitudinal direction along the first aperture, and wherein each ridge formed on the second aperture surface is so formed as to facilitate the movement of a suture in the first longitudinal direction and the first latitudinal direction along the second aperture and oppose the movement of the suture in the second longitudinal direction along the second aperture until pressure is applied to the suture in the second latitudinal direction, thereby disengaging the locking means and permitting the movement of the suture in the second longitudinal direction along the second aperture, wherein the first longitudinal direction along the first aperture and the second longitudinal direction along the second aperture are directed to the upper surface of the apparatus body.

12. The suture securing apparatus according to claim 1, wherein the suture securing apparatus is made from biocompatible materials.

13. A suture securing apparatus comprising:
(a) an apparatus body having a upper surface, a lower surface, an outer surface, and at least one aperture, the aperture having a longitudinal axis extending from the upper surface to the lower surface and defining an aperture surface, wherein a first longitudinal direction and a second longitudinal direction thereof each extends along the longitudinal axis in opposite directions,
the aperture consisting of an upper portion, a middle portion, and a lower portion, the upper portion bounded by the upper surface of the apparatus body and the middle portion, the middle portion bounded by the upper portion and the lower portion, and the lower portion bounded by the middle portion and the lower surface of the apparatus body, wherein the middle portion has a first surface and second surface opposing each other and is wider than either of the upper portion and the lower portion and forms a cavity therein; and
(b) a movable cam member disposed in the middle portion of the aperture, the cam member having an engagement end and a rotation end, the rotation end being wider than the width of the upper portion of the aperture thereof and the width of the lower portion of the aperture thereof and disposed near the second surface, and the engagement end disposed near the first surface;
wherein the cam member moves to an unengaged position to facilitate the movement of a suture threaded through the aperture in the first longitudinal direction along the aperture and moves to an engaged position to engage the suture threaded through the aperture in the second longitudinal direction by compressing the suture between the engagement end of the cam member and the first surface of the middle aperture to oppose the movement of the suture in the second longitudinal direction along the aperture.

14. The suture securing apparatus according to claim 13, wherein the first surface of the middle aperture comprises at least one ridge, each ridge so formed as to facilitate the movement of a suture in the first longitudinal direction along the aperture and oppose the movement of the suture in the second longitudinal direction along the aperture.

15. The suture securing apparatus according to claim 13, wherein the first surface of the middle aperture comprises a plurality of ridges, each ridge so formed as to facilitate the movement of a suture in the first longitudinal direction along the aperture and oppose the movement of the suture in the second longitudinal direction along the aperture.

16. The suture securing apparatus according to claim 13, wherein each ridge is formed from an elastic material.

17. The suture securing apparatus according to claim 13, wherein each ridge is formed from a rigid material.

18. The suture securing apparatus according to claim 13, wherein the engagement end of the cam member comprises serrations to grip the suture when engaged.

19. The suture securing apparatus according to claim 13, the apparatus body including a first aperture with a first movable cam member therein and a second aperture with a second movable cam member therein,
wherein the first movable cam member moves to an unengaged position to facilitate the movement of a suture threaded through the first aperture in the first longitudinal direction along the aperture and moves to an engaged position to engage the suture threaded through the first aperture in the second longitudinal direction by compressing the suture between the engagement end of the first movable cam member and the first surface of the middle aperture thereof to oppose the movement of the suture in a second longitudinal direction along the first aperture;
wherein the second movable cam member moves to an unengaged position to facilitate the movement of a suture threaded through the second aperture in the first longitudinal direction along the second aperture and moves to an engaged position to engage the suture threaded through the second aperture in the second longitudinal direction by compressing the suture between the engagement end of the first movable cam member and the first surface of the middle aperture thereof to oppose the movement of the suture in a second longitudinal direction along the second aperture; and
wherein the first longitudinal direction along the first aperture and the first longitudinal direction along the second aperture are both directed to the upper surface of the apparatus body.

20. The suture securing apparatus according to claim 19, wherein the first and second apertures and first and second cam members are mirror images of each other, as defined by a mirror plane equidistant from them.

21. The suture securing apparatus according to claim 13, the apparatus body including a first aperture with a first movable cam member therein and a second aperture with a second movable cam member therein,
wherein the first movable cam member moves to an unengaged position to facilitate the movement of a suture threaded through the first aperture in the first longitudinal direction along the aperture and moves to an engaged position to engage the suture threaded through the first aperture in the second longitudinal direction by compressing the suture between the engagement end of the first movable cam member and the first surface of the middle aperture thereof to oppose the movement of the suture in a second longitudinal direction along the first aperture;
wherein the second movable cam member moves to an unengaged position to facilitate the movement of a suture threaded through the second aperture in the first longitudinal direction along the second aperture and moves to an engaged position to engage the suture threaded through the second aperture in the second longitudinal direction by compressing the suture between the engagement end of the first movable cam member and the first surface of the middle aperture thereof to oppose the movement of the suture in a second longitudinal direction along the second aperture; and
wherein the first longitudinal direction along the first aperture and the second longitudinal direction along the second aperture are both directed to the upper surface of the apparatus body.

22. The suture securing apparatus according to claim 13, wherein the suture securing apparatus is made from biocompatible materials.

23. The suture securing apparatus according to claim 13, wherein the suture securing apparatus is made from biodegradable materials.

24. A securable medical prosthesis device comprising a medical prosthesis device in physical contact with at least one suture securing apparatus according to claim 2.

25. A securable medical prosthesis device comprising a medical prosthesis device in physical engagement with at least one suture securing apparatus according to claim 2.

26. The securable medical device according to claim 23, wherein the medical prosthesis device is a sewing ring implant shaped and sized for attachment to the inner surface of a native annulus, the sewing ring implant having a plurality of suture securing apparatuses distributed around the circumference of the sewing ring implant.

27. A securable medical prosthesis device comprising a medical prosthesis device integrally formed with at least one suture securing apparatus according to claim 2.

28. A securable medical prosthesis device comprising a medical prosthesis device in physical contact with at least one suture securing apparatus according to claim 13.

29. A securable medical prosthesis device comprising a medical prosthesis device in physical engagement with at least one suture securing apparatus according to claim 13.

30. A securable medical device according to claim 29, wherein the medical prosthesis device is a sewing ring implant shaped and sized for attachment to the inner surface of a native annulus, the sewing ring implant having a plurality of suture securing apparatuses distributed around the circumference of the sewing ring implant.

31. A securable medical prosthesis device comprising a medical prosthesis device integrally formed with at least one suture securing apparatus according to claim 13.

32. A suture securing apparatus comprising:

an apparatus body having a upper surface, a lower surface, an outer surface, a first aperture, and a second aperture, the first longitudinal direction of each aperture each being directed to the upper surface of the apparatus body, wherein each ridge formed on the first aperture surface and second aperture surface is so formed as to facilitate the movement of a suture in the first longitudinal direction and oppose the movement of the suture in the second longitudinal direction, each ridge is formed at an angle of about 45° to the longitudinal axis of the respective aperture, and the portion of each ridge extending farthest from the aperture surface is rounded, and wherein the first and second apertures are mirror images of each other, as defined by a mirror plane equidistant from them.

33. A suture securing apparatus comprising:

an apparatus body having a upper surface, a lower surface, an outer surface, and the apparatus body including a first aperture with a first movable cam member therein and a second aperture with a second movable cam member therein, the first longitudinal direction of each aperture each being directed to the upper surface of the apparatus body, wherein the first movable cam member and second movable cam member each moves to an unengaged position to facilitate the movement of a suture threaded through the respective aperture in the first longitudinal direction along the aperture and moves to an engaged position to engage the suture threaded through the respective aperture in the second longitudinal direction by compressing the suture between the engagement end of the respective movable cam member and the first surface of the middle aperture thereof to oppose the movement of the suture in a second longitudinal direction along the respective aperture; and wherein the first and second apertures and first and second cam members are mirror images of each other, as defined by a mirror plane equidistant from them.

34. The suture securing apparatus according to claim 1, wherein the first internal surface of the aperture is generally round and having sufficient diameter to accommodate a suture threaded therethrough, and the second internal surface is formed by an acute angular narrowing in the second latitudinal direction.

* * * * *

US006066160C1

(12) EX PARTE REEXAMINATION CERTIFICATE (9212th)
United States Patent
Colvin et al.

(10) Number: US 6,066,160 C1
(45) Certificate Issued: Aug. 21, 2012

(54) PASSIVE KNOTLESS SUTURE TERMINATOR FOR USE IN MINIMALLY INVASIVE SURGERY AND TO FACILITATE STANDARD TISSUE SECURING

(75) Inventors: Stephen Colvin, New York, NY (US); Eugene Grossi, New York, NY (US); Allan Katz, Freeport, NY (US); Paul Oddo, Freeport, NY (US)

(73) Assignee: Quickie, LLC, New York, NY (US)

Reexamination Request:
No. 90/006,460, Nov. 25, 2002
No. 90/007,085, Jun. 16, 2004

Reexamination Certificate for:
Patent No.: 6,066,160
Issued: May 23, 2000
Appl. No.: 09/198,087
Filed: Nov. 23, 1998

(51) Int. Cl.
*A61B 17/04* (2006.01)

(52) U.S. Cl. ............ 606/232; 606/151; 24/129 R; 24/130; 24/132 R

(58) Field of Classification Search ............... 24/132 R, 24/134 R, 134 KA, 132 AA, 132 WL; 623/2.38, 623/2.39, 2.4, 2.41, 50, 51, 13.14; 606/74, 606/103, 144, 232
See application file for complete search history.

(56) References Cited

To view the complete listing of prior art documents cited during the proceedings for Reexamination Control Numbers 90/006,460 and 90/007,085, please refer to the USPTO's public Patent Application Information Retrieval (PAIR) system under the Display References tab.

*Primary Examiner* — Jeffrey R. Jastrzab

(57) ABSTRACT

A suture securing apparatus comprising an apparatus body having a upper surface, a lower surface, an outer surface, and at least one aperture, the aperture having a longitudinal axis extending from the upper surface to the lower surface and defining an aperture surface, wherein a first longitudinal direction and a second longitudinal direction thereof each extends along the longitudinal axis in opposite directions, the aperture including an integral locking means for engaging a suture threaded therethrough.

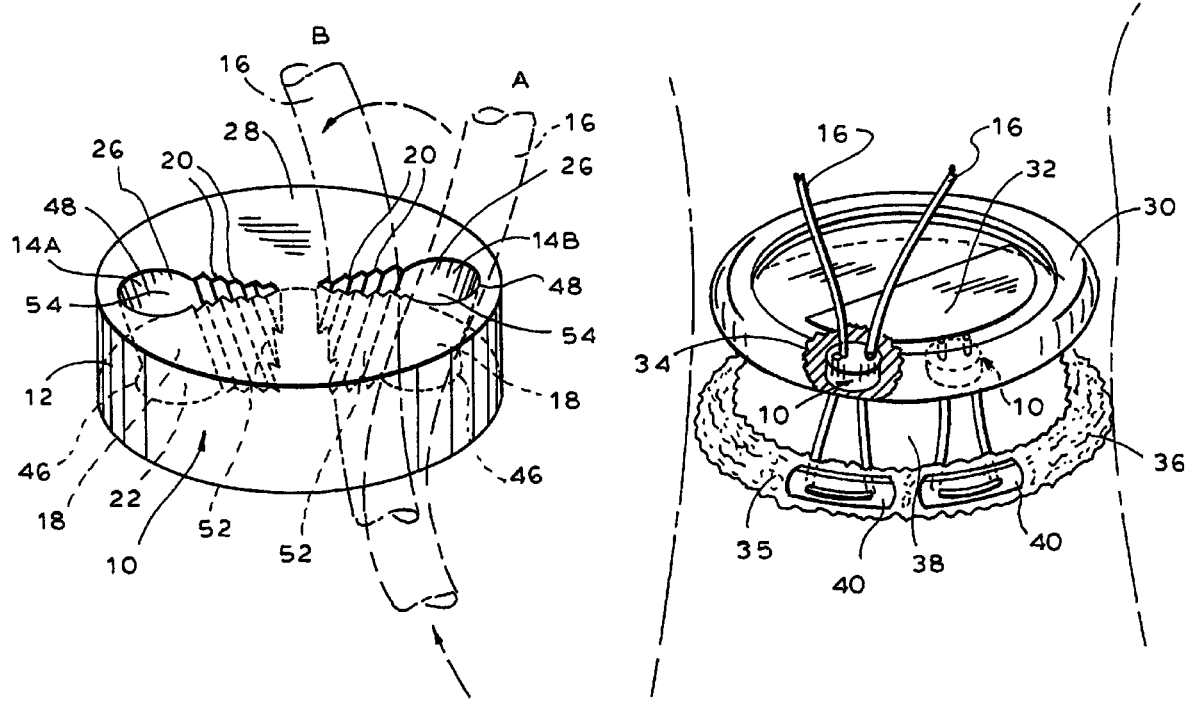

EX PARTE REEXAMINATION CERTIFICATE ISSUED UNDER 35 U.S.C. 307

THE PATENT IS HEREBY AMENDED AS INDICATED BELOW

AS A RESULT OF REEXAMINATION, IT HAS BEEN DETERMINED THAT:

The patentability of claims 1-34 is confirmed.
Other new claims 35-63 have been cancelled.

* * * * *